US006997181B2

(12) United States Patent
Fletcher

(10) Patent No.: US 6,997,181 B2
(45) Date of Patent: Feb. 14, 2006

(54) PERSONAL HYDRATION DEVICE

(75) Inventor: Paul Fletcher, Seattle, WA (US)

(73) Assignee: The Lighthouse for the Blind, Inc., Seattle, WA (US)

( * ) Notice: Subject to any disclaimer, the term of this patent is extended or adjusted under 35 U.S.C. 154(b) by 0 days.

(21) Appl. No.: 10/834,469

(22) Filed: Apr. 29, 2004

(65) Prior Publication Data

US 2005/0241641 A1 Nov. 3, 2005

(51) Int. Cl.
*A61M 15/00* (2006.01)
*A62B 9/02* (2006.01)

(52) U.S. Cl. .......................... 128/202.15; 128/205.24; 128/201.28; 128/206.29; 137/627.5; 137/614.04; 137/614.05

(58) Field of Classification Search ........... 128/205.24, 128/201.29, 201.28, 202.14, 206.29, 202.15, 128/204.26; 137/627.5, 614.04
See application file for complete search history.

(56) References Cited

U.S. PATENT DOCUMENTS 3,731,717 A * 5/1973 Potash ........................ 141/379
3,815,634 A * 6/1974 Dowdall et al. ......... 137/627.5
4,241,754 A * 12/1980 Moen ......................... 137/467
4,328,798 A * 5/1982 Isaacson ................ 128/202.27
4,523,604 A * 6/1985 Hutto ......................... 137/102
5,027,807 A * 7/1991 Wise et al. ............ 128/201.28
5,293,864 A * 3/1994 McFadden ............. 128/201.29
5,389,024 A * 2/1995 Chen ........................... 441/88
5,560,548 A * 10/1996 Mueller et al. ............. 239/442
5,727,714 A 3/1998 Fawcett
5,826,802 A 10/1998 Anderson et al.
6,227,199 B1 * 5/2001 Garofalo ................ 128/204.26
6,240,949 B1 6/2001 Gerstenberger
6,283,344 B1 9/2001 Bradley
6,325,116 B1 12/2001 Savage et al.
6,435,184 B1 8/2002 Ho
6,497,348 B1 12/2002 Forsman et al.
6,526,975 B1 3/2003 Chung
6,558,537 B1 5/2003 Herrington et al.
6,622,988 B1 9/2003 Gill
6,668,861 B1 12/2003 Williams
6,675,833 B1 * 1/2004 Maldavs ................ 137/614.05
6,675,998 B1 1/2004 Forsman et al.

* cited by examiner

*Primary Examiner*—Henry Bennett
*Assistant Examiner*—Andrew Bunin
(74) *Attorney, Agent, or Firm*—Christensen O'Connor Johnson Kindness PLLC

(57) ABSTRACT

A personal hydration device providing fluid delivery to an external mouthpiece and a gas mask mouthpiece is disclosed. The personal hydration device includes a container having an exit port and an exit valve, a diverter valve, an external mouthpiece, a gas mask with a gas mask mouthpiece, and three hoses connecting these elements together. The diverter valve has a body, including one inlet and two outlets, and a spool moveably mounted within the body. The spool is moveable between a first position and a second position, and normally biased toward the first position. When in the first position, the first outlet is in an open position and fluid is delivered to the external mouthpiece. When in the second position, the first outlet is in a closed position and fluid is delivered to the gas mask mouthpiece.

10 Claims, 3 Drawing Sheets

PERSONAL HYDRATION DEVICE

FIELD OF THE INVENTION

The present invention relates to personal hydration devices, and more specifically to personal hydration devices configured to be interchangeable between providing fluid delivery from a container to two or more outlets, for example, an external mouthpiece and a gas mask mouthpiece.

BACKGROUND OF THE INVENTION

In a chemically hazardous environment, it is often necessary for an individual wearing a protective mask, for example, a face mask or a gas mask, to drink water or other fluids from a canteen or another closed fluid storage container without removing the protective mask or contaminating the fluid.

Past devices designed for the transfer of fluids from a closed canteen or storage vessel to a person wearing a protective mask do not adequately prevent contamination of the fluid or the individual. In addition, past devices have also contained excessive parts. Excessive parts can increase both the susceptibility of the device to damage or the manufacturing costs. Past devices are described in U.S. Pat. No. 6,325,116 entitled, "Adaptor for Providing Fluid Control Between a Canteen and a Face Mask Fluid Tube," to Savage et al., issued Dec. 4, 2001.

Accordingly, there exists a need for a fluid delivery system that prevents harmful contamination. Further, there exists a need for a fluid delivery system that is simple in design, economical to manufacture, readily adaptable to protective equipment already in widespread use, and manufactured in a manner and with materials which allow the integrity of the fluid delivery system to be maintained, in all inclement, chemically or biologically hostile, or combat environments.

SUMMARY OF THE INVENTION

A personal hydration device according to the present invention is interchangeable between providing fluid delivery to two outlets. The personal hydration device includes a container having an exit port and an exit valve, and a diverter valve. The diverter valve has a body, including an inlet, a first outlet, a second outlet, and a spool moveably mounted within the body. The spool is moveable between a first position and a second position. When in the first position, the first outlet is in an open position and the second outlet is in a closed position. When in the second position, the first outlet is in a closed position and the second outlet is in an open position. The diverter valve spool is normally biased toward the first position. The diverter valve, however, is urged to the second position.

The personal hydration device can further include an external mouthpiece, a gas mask with a gas mask mouthpiece, and three hoses connecting these elements together, a container hose, an external mouthpiece hose, and a gas mask mouthpiece hose.

The container hose has a first end and a second end. The first end of the container hose is connectable to the exit port of the container, and the second end is connectable to the inlet of the diverter valve. The external mouthpiece hose has a first end and a second end. The first end of the external mouthpiece hose is connectable to the first outlet of the diverter valve, and the second end is connectable to an external mouthpiece. Finally, the gas mask mouthpiece hose has a first end and a second end. The first end of the gas mask mouthpiece hose is connectable to the second outlet of the diverter valve, and the second end is connectable to the gas mask mouthpiece. The diverter valve remains in the first position when the gas mask mouthpiece hose is not connected to the diverter valve, but the diverter valve is urged to the second position when the gas mask mouthpiece hose is connected to the diverter valve. When disconnected, the diverter valve returns to the first position.

In a preferred embodiment, the first end of the gas mask mouthpiece hose is the male coupling half of a coupler socket, and the second outlet of the diverter valve is the female coupling half of a coupler socket, the male half and the female half being releasably connectable to form a coupler socket.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
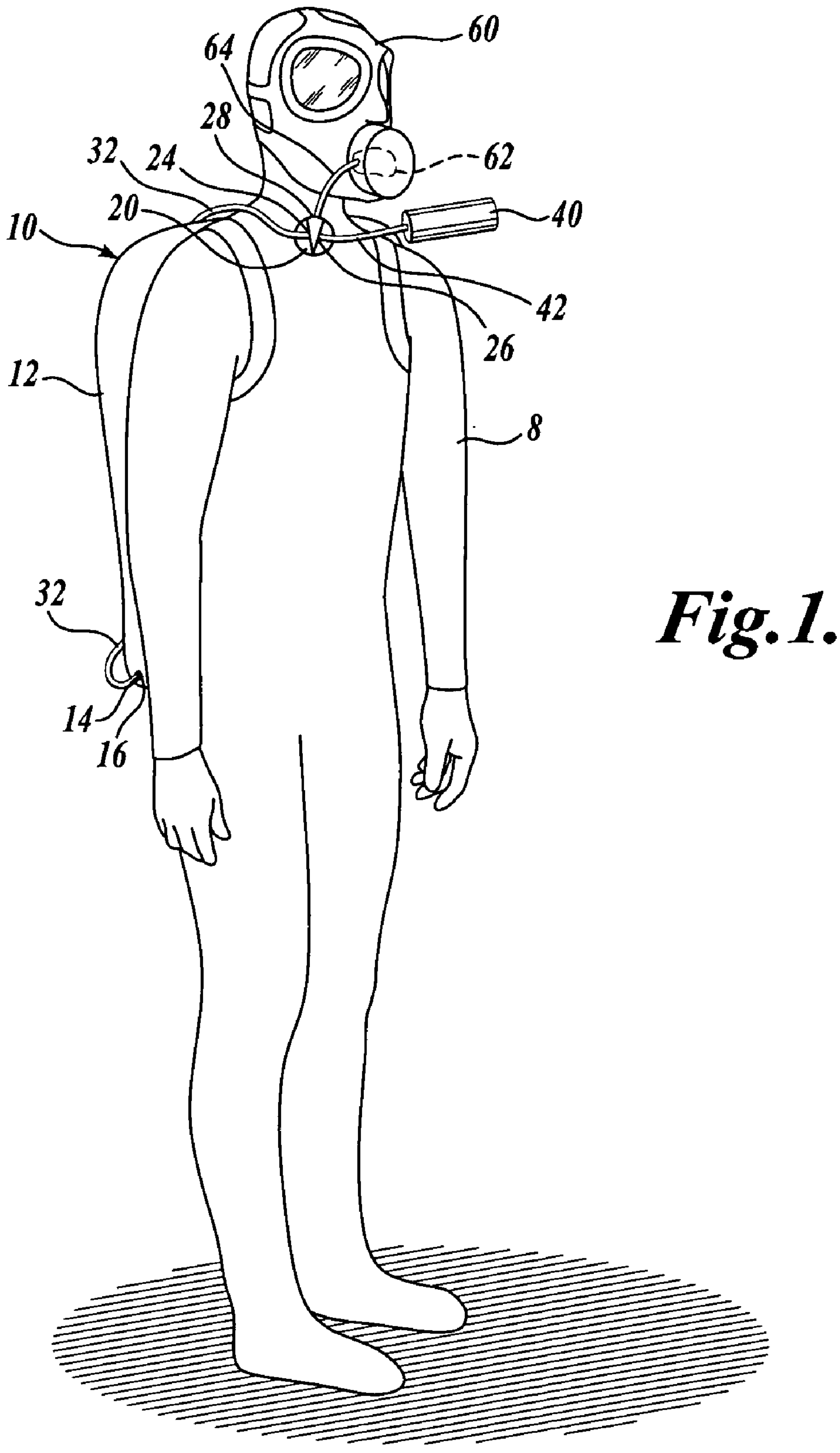
FIG. 1 is a perspective view of a user wearing a hydration pack with a diverter valve for interchangeably providing fluid delivery from a container to an external mouthpiece and a gas mask mouthpiece according to the present invention.

One embodiment of the present invention is personal hydration device that is interchangeable between providing fluid delivery from a container to a first outlet and to a second outlet. Referring to FIG. 1, the preferred embodiment of the personal hydration device 10 for use in providing fluid delivery to an external mouthpiece 40 or, in a second configuration, providing fluid delivery to a gas mask mouthpiece 62 worn and used by a user 8.

The personal hydration device 10 includes a container 12 for holding water or any other fluid. The container 12 is worn on the body of the user 8, such as on the back or torso of the user 8 (held by an outer pack with straps or a harness). The container 12 also can be worn on the user's belt or otherwise attached to the user's clothing. In addition, the container 12 can be carried by the user 8.

The container 12 of the present invention can be a hydration bag. Hydration bags and/or personal hydration systems are known to one of ordinary skill in the art and are also commercially available. Personal hydration systems typically have a bag reservoir or another type of reservoir, which can be resilient or rigid. Most of these hydration devices provide a means for drinking fluid stored in the device. For example, a flexible hose can be connected to the reservoir through an exit port at one end, terminating in a mouthpiece at the other end. The hose can be long enough to allow the mouthpiece to be carried in the user's mouth to enable the user to draw fluid from the reservoir at will.

Examples of hydration devices are disclosed in U.S. Pat. No. 5,727,714, entitled "Personal Hydration Device With Improved Exit Valve," to Fawcett, issued Mar. 17, 1998;

U.S. Pat. No. 5,060,833, entitled "Camel Back," to Edison et al., issued Oct. 29, 1991; and U.S. Pat. No. 5,085,349, entitled "Resilient Valve and Dispensing System for Bicyclists," to Fawcett, issued Feb. 4, 1992, the disclosures of the patents are herein incorporated by reference in their entirety. As described in the Fawcett '714 reference, the flexible plastic container can be formed by welding two sheets of a flexible plastic material together around their periphery to form a reservoir.

One commercially available hydration bag, sold by Mountain Safety Research, Inc., of Seattle, Wash., (see, e.g., U.S. Pat. No. D352,359), comprises a durable, abrasion resistant 500 denier CORDURA.RTM. nylon E.I. du Pont de Nemours and Co., Wilmington, Del.) outer layer bonded to a food-grade polyurethane inner layer. This bag is collapsible, has multiple grommets laced with webbing for easy hanging and carrying and a three-way cap for ease of drinking, filling and pouring. This bag has a dry weight of 5.4 ounces (153 grams) and a capacity of four liters. Commercial hydration systems optionally comprise a variety of accessories, such as, but not limited to, bite valves, spigot valves, shower kits, and cases.

Bag and non-bag reservoir systems known in the art are within the scope of the present invention. For example, the container 12 also can be a rigid container, for example, a canteen manufactured from metal, such as aluminum or any other metal or metal alloy, or rigid plastic, such as a polyester or polycarbonate, using conventional injection molding or blow techniques. The container further can be insulated to keep the fluid at a desired temperature, or can include radiation reflective, radiation absorbing surfaces, and/or evaporative cooling surfaces. The container can be sized to hold any designated maximum amount of fluid.

The container 12 of the present invention includes an exit port 14 and an exit valve 16 for controlling the output flow of fluid from the container 12. The exit valve 16 prevents the free flow of fluid from the container 12, but the exit valve 16 releases fluid when there is demand from the user 8. Demand from the user includes suction on a mouthpiece at the end of a connecting hose by a user.

A representative exit valve 16 for a hydration bag is also described in the Fawcett '714 reference. The exit valve can include a generally rectangular base flange with a round end. The base flange is welded to a side of the bag to secure the exit valve to the bag. The exit valve can be generally welded at the bottom of the bag so that the exit valve can draw essentially all of the fluid out of the bag. The exit valve 16 can include a tube mount projecting outward to form an exit port and provide an attachment tube for a hose. The user 8 draws fluid from the container 12 by creating suction on the exit valve 16.

Figure 2:
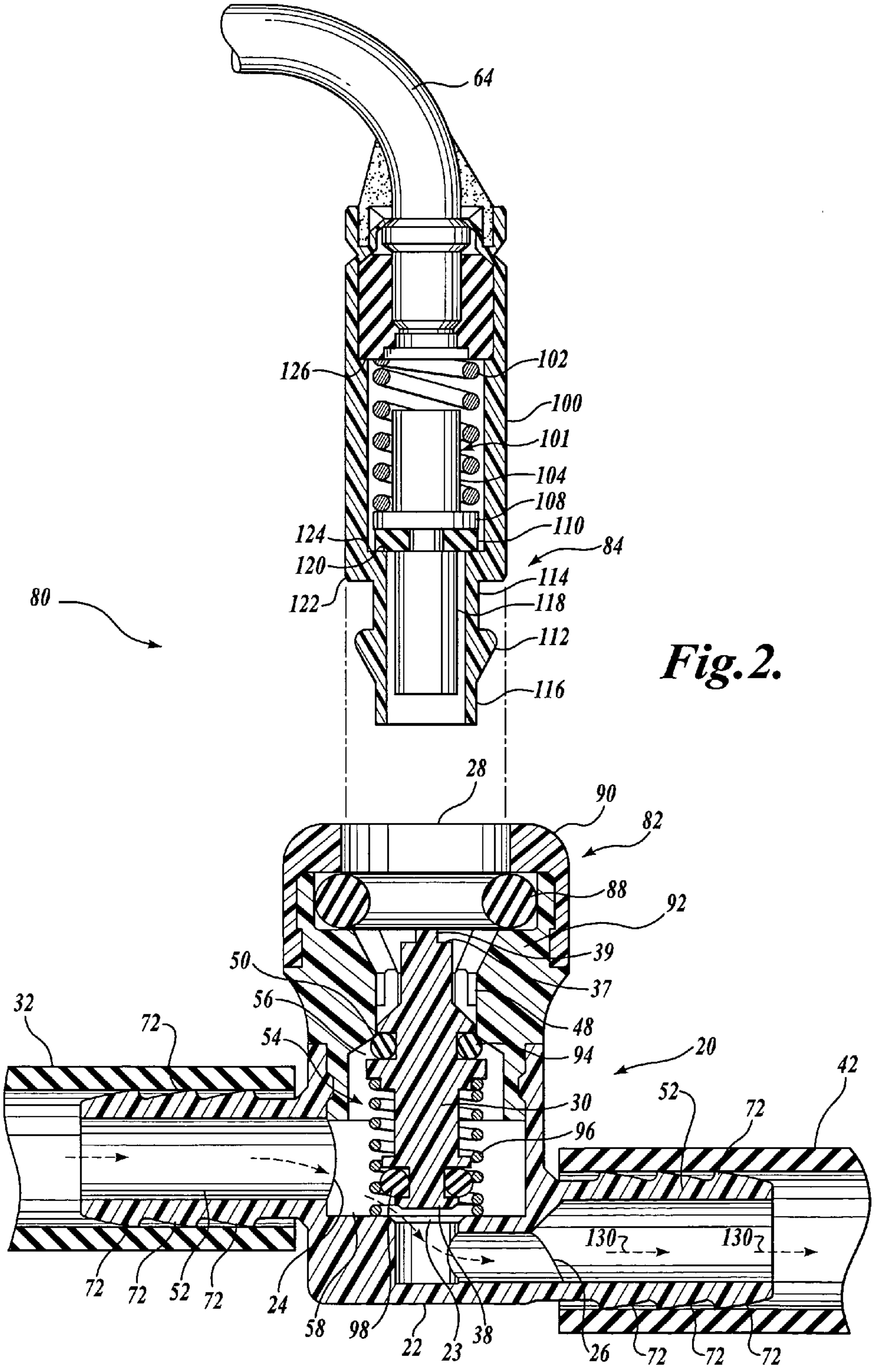
FIG. 2 is a cross-sectional view of a diverter valve according to the present invention in a first position.

Referring to FIGS. 1 and 2, the personal hydration device 10 further includes a diverter valve 20 having an inlet 24, and at least a first outlet 26 and a second outlet 28. The diverter valve inlet 24 and the container exit port 14 are connected by a container hose 32, having a first end and a second end. Fluid can flow from the container exit port 14 through the container hose 32 to the diverter valve inlet 24. The diverter valve inlet 24 can include a tube mount 52 projecting from the inlet port 24. When the diverter valve 20 is in a first position, fluid can flow along a first passage 130 into the diverter valve inlet 24 and out the diverter valve first outlet 26.

Referring now to FIG. 1, the personal hydration device 10 further includes an external mouthpiece 40 for fluid delivery thereto. The external mouthpiece 40 is connected to the diverter valve first outlet 26 by an external mouthpiece hose 42, having a first end and a second end. The first end of the external mouthpiece hose 42 is connected to the diverter valve first outlet 26. The second end of the external mouthpiece hose 42 is connected to the external mouthpiece 40.

Referring to FIG. 2, the diverter valve first outlet 26 can include a tube mount 52 projecting from the first outlet port 26 for releasably connecting the diverter valve 20 to the external mouthpiece hose 42. The external mouthpiece 40 can also include a tube mount 52. Alternatively, the mouthpiece 40 can be integrated with the external mouthpiece hose 42, for example, welded together. When the diverter valve 20 is in a first position, a first passage 130 allows for fluid travel from the container exit port 14, through the container hose 32 to the diverter valve inlet 24, out the diverter valve first outlet 26, through the external mouthpiece hose 42, and to the external mouthpiece 40.

Mouthpieces for personal hydration devices are well-known in the art. See, for example, U.S. Pat. No. 6,497,348, entitled "Hydration System With Improved Fluid Delivery System," to Forsman et al., issued Dec. 24, 2002; and U.S. Pat. No. 6,622,988, entitled "Mouthpiece for Drinking," to Gill, issued Sep. 23, 2003, both herein incorporated by reference in their entirety. The external mouthpiece 40 can be a bite-actuated or mouth-actuated mouthpiece that is normally in a closed position, preventing fluid from being dispensed from the mouthpiece 40. The mouthpiece 40 can be activated, by bite or mouth action, into an open position. When the mouthpiece 40 is in the open position, the user 8 draws fluid from the container 12 to the mouthpiece 40 by creating suction on the mouthpiece 40. The bite- or mouth-actuated mouthpiece 40 can be biased or otherwise configured to normally be in the closed position. Furthermore, the mouthpiece 40 can have a "locked" position to prevent the mouthpiece from opening, even if activated by bite or mouth action, to prevent fluid passage without first becoming "unlocked."

Referring to FIG. 1, the personal hydration device 10 further includes a gas mask 60 with a gas mask mouthpiece 62. The gas mask mouthpiece 62 is connected to the diverter valve second outlet 28 by a gas mask mouthpiece hose 64, having a first end and a second end. The first end of the gas mask mouthpiece hose 64 is connected to the diverter valve second outlet 28. The second end of the gas mask mouthpiece hose 64 is connected to the gas mask mouthpiece 62. The gas mask mouthpiece 62 can include a tube mount 52 for releasably connecting the second end of the gas mask mouthpiece hose 64 to the gas mask mouthpiece 62. Alternatively, the gas mask mouthpiece 62 can be integrated with the gas mask mouthpiece hose 64.

The gas mask 60 can be of the type conventionally used for protection from chemical, biological, nuclear, or other environment contaminants. See, for example, U.S. Pat. No. 6,435,184, entitled "Gas Mask Structure," to Ho, issued Aug. 20, 2002, included herein by reference in its entirety. On the inside of the gas mask 60, a drinking mouthpiece 62 for fluid delivery is provided. The gas mask mouthpiece 62 can be similar to the external mouthpiece 40, as described above. The gas mask mouthpiece 62 can have closed and "locked" positions to prevent the entry of contamination into the gas mask 60 through the gas mask mouthpiece 62.

The diverter valve 20 is preferably a two-position valve. In a first position, the diverter valve 20 provides fluid delivery to a first outlet 26. In a second position, the diverter valve 20 provides fluid delivery to a second outlet 28. The diverter valve 20 is preferably a poppet valve or spool valve. In one embodiment, referring to FIGS. 2 and 3, the diverter valve 20 includes a spool 30, moveably mounted within a spool chamber 54, having a first end 56 and a second end 58. A diverter valve neck 48 is connected to the spool chamber first end 56, and a diverter valve base 22 is connected to the spool chamber second end 58. The diverter valve neck 48 can be a part of a female half 82 of a coupling socket 80. The diverter valve base 22 has an annular opening 23, through which fluid travels to the diverter valve second outlet 28. The spool 30 has a first end 37 and a second end 38. The spool first end 37 is the end closest to the diverter valve second outlet 28, and it extends into the diverter valve neck 48. The spool has a stem 39 attached at the first end 37. The spool second end 38 is the end closest to the diverter valve base 22. The diverter valve neck 48 has a smaller inner diameter than the spool chamber 54. Therefore, there is an inwardly facing spool chamber annular shoulder 50 at the first end of the spool chamber 56 where the spool chamber connects with the diverter valve neck 48.

Figure 3:
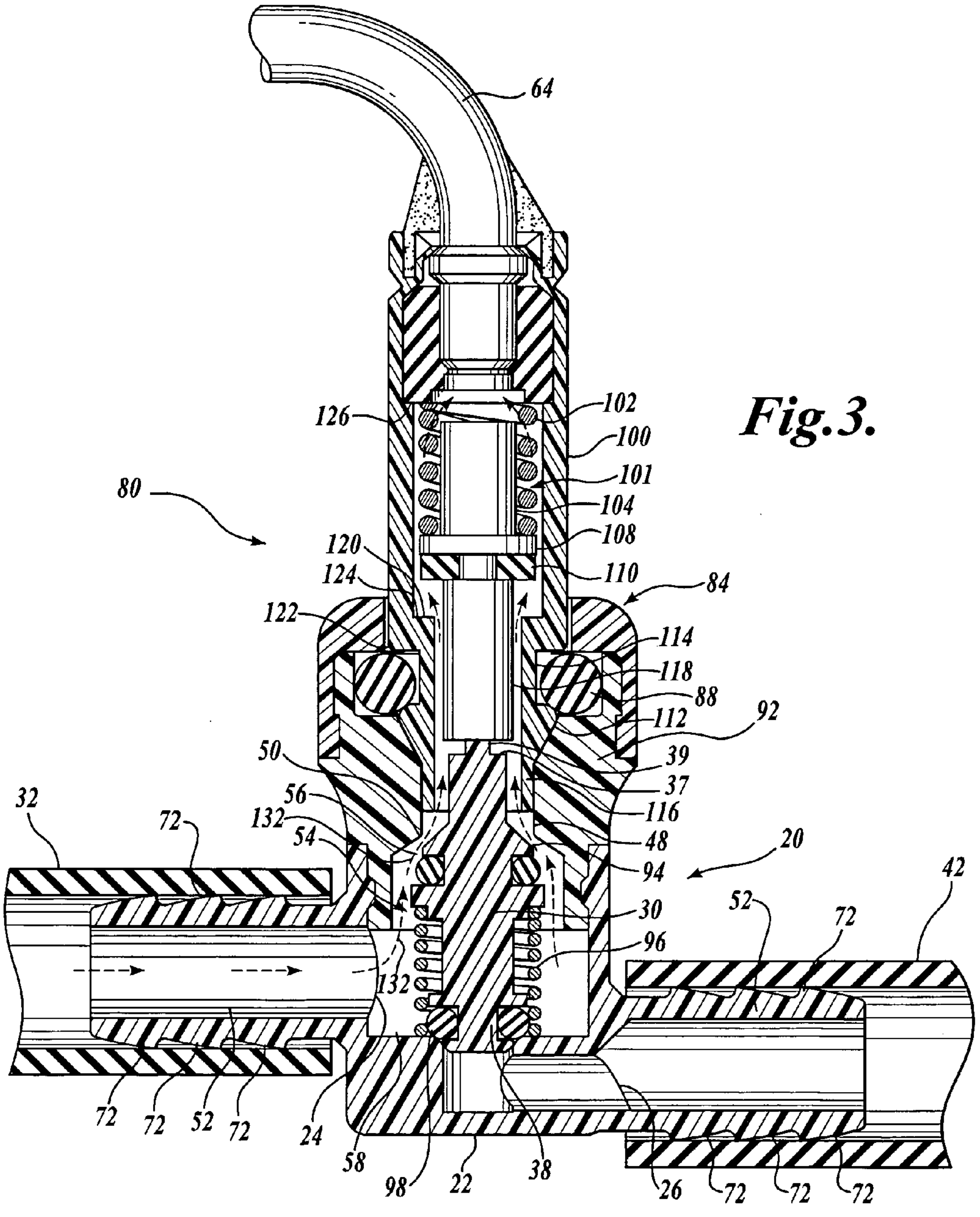
FIG. 3 is a cross-sectional view of a diverter valve according to the present invention in a second position.

Being moveably mounted within the spool chamber 54, the spool 30 is moveable between a first position, referring to FIG. 2, and a second position, referring to FIG. 3. The spool 30 includes first and second seals 94 and 98. The spool first and second seals 94 and 98 can be flexible seals, such as O-ring seals. When the spool 30 is in a first position, referring to FIG. 2, the spool first seal 94 is urged against and seals against the spool chamber shoulder 50, and a first passage 130 is created from the diverter valve inlet 24, between the spool 30 and the annular opening 23 in the diverter valve base 22, and to the diverter valve first outlet 26. Thus, when the diverter valve 20 is in the first position, there is a first passage 130 through the first outlet 26, but not through the second outlet 28.

When the spool 30 is in a second position, referring to FIG. 3, the spool second seal 98 is urged against and seals off the annular opening in the diverter valve base 22, and a second passage 132 is created from the diverter valve inlet 24, around the spool 30, and through the diverter valve second outlet 28. Thus, when the diverter valve 20 is in the second position, there is a second passage 132 through the second outlet 28, but not through the first outlet 26.

Referring to FIG. 2, the spool 30 within the diverter valve 20 further includes means to normally bias it in the first position. "Biasing means" includes the spool spring 96, which urges the spool 30 to the first position, away from the valve base 22 and toward the valve second outlet 28. Although the spool 30 is normally biased to the first position, the spool 30 is urged to the second position, referring to FIG. 3, when the gas mask mouthpiece hose 64 is connected to the diverter valve second outlet 28. "Biasing means" is not limited to springs, but also includes pressurized bladders and the like.

Referring to FIGS. 2 and 3, the gas mask mouthpiece hose 64 is preferably connected to the diverter valve second outlet 28 at a coupler socket 80 with male and female halves 82 and 84 that couple together. The diverter valve second outlet 28 is preferably part of the female coupling half 82. The female coupling half 82 of the coupler socket 80 is designed to receive a male coupling half 84. One type of coupler socket well-known to one of ordinary skill in the art includes a cylindrical body with an internal poppet spool. See, for example, U.S. Pat. No. 6,675,833, entitled "Connect Under Pressure Coupling," to Maldavs, issued Jan. 13, 2004.

In the preferred embodiment, referring to FIG. 2, the female coupling half 82 includes the female cylindrical body 92, the female fitting 90, and the female annular seal 88 lodged between the female cylindrical body 92 and the female fitting 90. The female annular seal 88 can be a flexible seal, such as an O-ring seal.

Still referring to FIG. 2, the spool 30 is biased into the first position when the male coupling half 84 is not connected to the female coupling half 82. When fluid is in the diverter valve 20, internal fluid pressure in the spool chamber 54, pushing against the spool second end 38 and the spool spring 96, can further urge the spool 30 away from diverter valve base 22 and against the spool chamber shoulder 50. In addition to the spool spring 96, the fluid pressure helps prevent fluid leakage from the valve second outlet 28 when the coupling halves 82 and 84 are disconnected.

The male coupling half 84 can be attached to the first end of the gas mask mouthpiece hose 64. The male coupling half 84 can include a tube mount 52 for releasably connecting the first end of the gas mask mouthpiece hose 64 to the male coupling half 84. Alternatively, the male coupling half 84 can be integrated with the gas mask mouthpiece hose 64, as shown in the illustrated embodiment of FIGS. 2 and 3.

Referring to FIG. 2, the male coupling half 84 includes an outer cylindrical body 100 having a first end 124 and a second end 126, a protruding male cylindrical connector 116, and an inner plug assembly 101. The male inner plug assembly 101 within the male cylindrical body 100 includes a first male spool 104. The first male spool 104 is further attached to a male flange 108, a male annular seal 110, and a second male spool 118. The male inner plug assembly 101 is spring-biased by a male spring 102 toward the first end 124 of the male cylindrical body 100. The male annular seal 110 is greater in diameter than the second male spool 118 and rests, when biased toward the first end 124, on a first inwardly facing annular shoulder 120 of the male cylindrical connector 116. The male annular seal 110 is therefore biased to a closed position against the first end 124 of the male cylindrical body 100.

The male cylindrical connector 116 is smaller is diameter than the male cylindrical body 100, forming a second outwardly-facing annular shoulder 122. The male cylindrical connector has an annular ridge 112 and an annular groove 114, the annular groove 114 lies between the annular ridge 112 and the second annular shoulder 122.

Referring to FIG. 3, the male cylindrical connector 116 can be received within the female fitting 90 and the female cylindrical body 92. The male annular ridge 112 is larger in diameter than the female annular seal 88. Therefore, force must be applied to insert the male annular ridge 112 inside the female cylindrical body 92 past the female annular seal 88. Once the male annular ridge 112 passes the female annular seal 88, the male annular groove 114 then rests on the female annular seal 88. The male annular ridge 112 and the second male annular shoulder 122 prevent the coupling halves 82 and 84 from moving or disconnecting during normal use.

Referring still to FIG. 3, when the coupling halves 82 and 84 are coupled together, the female spool 30 is urged against the spool second seal 98, closing off the annular opening in the diverter valve base 22, sealing the first passage 130 between the female spool 30 and the diverter valve base 22 toward the diverter valve first outlet 26, and opening the second passage 132 toward the diverter valve second outlet 28. When the coupling halves 82 and 84 are joined, the male inner plug assembly 101 is urged away from the first end 124 of the male cylindrical body 100 and toward the second end 126 of the male cylindrical body 100, opening the second passage 132. Therefore, during the coupling of the female and male coupling halves 82 and 84, the male inner plug assembly 101 moves rearwardly, and opens the second passage 132 into the gas mask mouthpiece hose 64, providing fluid delivery to the gas mask mouthpiece 62.

The male coupling half 84 and the female coupling half 82 are releasably connectable. To uncouple the male coupling half 84 from the female coupling half 82, a force equal to the force used to couple the halves together must be used to pull the halves apart. The male annular ridge 112 on the cylindrical connector can be forced over the female seal 88, and the two coupling halves 82 and 84 will disconnect. In another embodiment, the coupler socket 80 can use a locking collar to release the coupling halves by manual manipulation. Locking collars are well-known in the art. A suitable locking collar is described in the Maldavs '833 patent.

As the male coupling half 84 is removed from the female coupling half 82, the spool 30 in the female coupling half 82 and the male inner plug assembly 101 in the male coupling half 84 are biased to their normal, closed positions. Biasing the coupling halves to closed positions prevents fluid flow through the uncoupled halves. In this manner, no contamination enters into the gas mask mouthpiece hose 64, extending to the gas mask mouthpiece 62, or into the diverter valve 20. Thus, the fluid within the personal hydration device 10 always remains clean and uncontaminated.

To further prevent contamination, the male coupling half 84 can have a covering that is removed only when the male coupling half 84 is to be inserted in the female coupling half 82 to provide fluid delivery to the gas mask mouthpiece 62. Accordingly, the female coupling half 82 can also have a covering that is removed only when the male coupling half 84 is to be inserted in the female coupling half 82. These coverings provide additional protection from the external environment when the gas mask 60 is not is use, and can easily by put on and taken off.

The first, second, and gas mask mouthpiece hoses 32, 42, and 64 can be made from tubing of a semi-rigid plastic, such as polyvinylchloride (PVC), nylon, or teflon. Semi-rigid tubing provides enough flexibility to accommodate handling, storage, and use, but also enough rigidity so that it does not become snared or dislodged from use. The semi-rigid tubing can be sized and shaped to properly allow the user to wear or use the personal hydration device comfortably and to draw enough fluid through the tubing. The tubing can be mounted along the container, a user's belt, a user's protective suit, or upon any other surface. The tubing can be mounted using adhesive or hook-and-fastener attachment pads, snap clips, a molded construction, or any other type of fastener.

As described above, the hoses connect to tube mounts 52 on the exit valve 16, the diverter valve inlet 24, the diverter valve outlets 26 and 28, the external mouthpiece 40, and the gas mask mouthpiece 62. A tube mount 52 is a short tube sized to be the same size or smaller than a hose to create a tight fit within a hose. A tube mount 52 can include at least one barb 72 to enhance the grip of a hose on the tube mount 52. The number of barbs 72 can vary, for example, depending upon the length of the tube mounts 52, or the desired force required to remove the tube from the tube mount 52. Because the hoses are formed from flexible material, they still can be removed from any of the tubes mounts 52, as required, for cleaning, repair, or replacement. It is also within the scope of the invention that tube mounts 52 can be formed without ribs or barbs 72, in which case the mounting structure can be a friction fit between the end of the hose and the tube mount 52. Further examples of other suitable mounting structures include clamps or ties that bind the end of the hoses to tube mounts, as well as other connectors. Although the hoses are preferably releasably attached to permit removal for cleaning, repair, or replacement, they also can be permanently attached by permanent adhesives or by being integrally formed with the structure of the personal hydration system.

Referring to FIG. 2, when the spool 30 is in the first position, fluid can be delivered to the diverter valve 20 at the diverter valve inlet 24, through the diverter valve first outlet 26, and to the external mouthpiece 40 through the external mouthpiece hose 42. A user 8 unlocks and bites, or otherwise activate, the external mouthpiece 40 into an open position. The user 8 then draws fluid from the container 12 by sucking on the external mouthpiece 40 to open the container exit valve 16 at the container exit port 14. Fluid will flow from the container exit port 14 to the diverter valve inlet 24, through the first passage 130, to the diverter valve first outlet 26, through the external mouthpiece hose 42 to the external mouthpiece 40, and into the mouth of the user 8. When the spool 30 is in the first position, no fluid is delivered to the second outlet 28 or the gas mask mouthpiece 62.

Referring to FIG. 3, when the spool 30 is urged in the second position, the first outlet 26 is in a closed position and the second outlet 28 is in an open position. When the spool 30 is in the second position, fluid can be delivered to the gas mask mouthpiece 62. A user 8 unlocks and bites, or otherwise activate, the gas mask mouthpiece 62 into an open position. The user 8 then draws fluid from the container 12 by sucking on the gas mask mouthpiece 82 to open the container exit valve 16 at the container exit port 14. Fluid will flow from the container exit port 14 to the diverter valve inlet 24, through the second passage 132, to the diverter valve second outlet 28, through the gas mask mouthpiece hose 64 to the gas mask mouthpiece 62, and into the mouth of the user 8. When the spool 30 is in the second position, no fluid is delivered to the first outlet 26 or the external mouthpiece 40.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A personal hydration device comprising:

a container having an exit port and an exit valve;

a diverter valve having a body comprising an inlet, a first outlet, a second outlet, and a spool moveably mounted within the body, the spool being moveable between a first position and a second position, wherein in the first position the first outlet is in an open position and the second outlet is in a closed position, and wherein in the second position the first outlet is in a closed position and the second outlet is in an open position;

means for biasing the spool toward the first position;

means for urging the spool toward the second position; and a container hose having a first end and a second end, the first end being connected to the exit port of the container, and the second end being connected to the inlet of the diverter valve.

2. The personal hydration device of claim 1, further comprising an external mouthpiece hose having a first end and a second end, the first end being connected to the first outlet of the diverter valve, and the second end being connected to an external mouthpiece.

3. The personal hydration device of claim 1, further comprising a gas mask having a gas mask mouthpiece, and a gas mask mouthpiece hose, having a first end and a second end, the first end being connected to the second outlet of the diverter valve, and the second end being connected to the gas mask mouthpiece.

4. The personal hydration device of claim 3, wherein the first end of the gas mask mouthpiece hose is the male coupling half of a coupler socket, and the second outlet of the diverter valve is the female coupling half of a coupler socket, the male half and the female half being releasably connected to form a coupler socket.

5. The personal hydration device of claim 1, wherein the diverter valve is in the first position when the gas mask mouthpiece hose is not connected to the diverter valve, and wherein the diverter valve is urged to the second position when the gas mask mouthpiece hose is connected to the diverter valve.

6. In combination with a personal hydration device including a container having an exit port and an exit valve, and a container hose having a first end and a second end, the first end being connected to the exit port of the container, the improvement comprising:

a diverter valve connected to the first end of the container hose, having a body comprising an inlet, a first outlet, a second outlet, and a spool moveably mounted within the body, the spool being moveable between a first position and a second position, wherein in the first position the first outlet is in an open position and the second outlet is in a closed position, and wherein in the second position the first outlet is in a closed position and the second outlet is in an open position;

means for biasing the spool toward the first position; and means for urging the spool toward the second position.

7. A personal hydration device for use in providing fluid delivery to an external mouthpiece and a gas mask mouthpiece, comprising:

a container having an exit port and an exit valve;

a diverter valve having a body comprising an inlet, a first outlet, a second outlet, and a spool moveably mounted within the body, the spool being moveable between a first position and a second position, wherein in the first position the first outlet is in an open position and the second outlet is in a closed position, and wherein in the second position the first outlet is in a closed position and the second outlet is in an open position;

means for biasing the spool toward the first position;

a container hose having a first end and a second end, the first end being connected to the exit port of the container, and the second end being connected to the inlet of the diverter valve;

an external mouthpiece hose having a first end and a second end, the first end being connected to the first outlet of the diverter valve, and the second end being connected to an external mouthpiece;

a gas mask having a gas mask mouthpiece;

a gas mask mouthpiece hose, having a first end and a second end, the first end being connected to the second outlet of the diverter valve, and the second end being connected to the gas mask mouthpiece;

the diverter valve being in the first position when the gas mask mouthpiece hose is not connected to the diverter valve; and the diverter valve being urged to the second position when the gas mask mouthpiece hose is connected to the diverter valve.

8. The personal hydration device of claim 7, wherein the first end of the gas mask mouthpiece hose is the male coupling half of a coupler socket, and the second outlet of the diverter valve is the female coupling half of a coupler socket, the male half and the female half being releasably connected to form a coupler socket.

9. A personal hydration device for use in providing fluid delivery to an external mouthpiece and a gas mask mouthpiece, comprising:

a container having an exit port and an exit valve;

a diverter valve having a body comprising an inlet, a first outlet, a second outlet, and a spool moveably mounted within the body, the spool being moveable between a first position and a second position, wherein in the first position the first outlet is in an open position and the second outlet is in a closed position, and wherein in the second position the first outlet is in a closed position and the second outlet is in an open position;

a spring biasing the spool toward the first position;

a container hose having a first end and a second end, the first end being connected to the exit port of the container, and the second end being connected to the inlet of the diverter valve;

an external mouthpiece hose having a first end and a second end, the first end being connected to the first outlet of the diverter valve, and the second end being connected to an external mouthpiece;

a gas mask having a gas mask mouthpiece;

a gas mask mouthpiece hose, having a first end and a second end, the first end being connected to the second outlet of the diverter valve, and the second end being connected to the gas mask mouthpiece;

the diverter valve being in the first position when the gas mask mouthpiece hose is not connected to the diverter valve; and the diverter valve being urged to the second position when the gas mask mouthpiece hose is connected to the diverter valve.

10. The personal hydration device of claim 9, wherein the first end of the gas mask mouthpiece hose is the male coupling half of a coupler socket, and the second outlet of the diverter valve is the female coupling half of a coupler socket, the male half and the female half being releasably connected to form a coupler socket.

* * * * *